United States Patent
Im et al.

(10) Patent No.: US 10,500,174 B2
(45) Date of Patent: Dec. 10, 2019

(54) PHARMACEUTICAL COMPOSITION FOR PREVENTING OR TREATING DEGENERATIVE BRAIN DISEASE

(71) Applicant: SOONCHUNHYANG UNIVERSITY INDUSTRY ACADEMY COOPERATION FOUNDATION, Asan-si, Chungcheongnam-do (KR)

(72) Inventors: Jungkyun Im, Asan-si (KR); Goutam Biswas, Delhi (IN)

(73) Assignee: SOONCHUNHYANG UNIVERSITY INDUSTRY ACADEMY COOPERATION FOUNDATION, Asan-si (KR)

( * ) Notice: Subject to any disclaimer, the term of this patent is extended or adjusted under 35 U.S.C. 154(b) by 0 days.

(21) Appl. No.: 16/361,129

(22) Filed: Mar. 21, 2019

(65) Prior Publication Data
US 2019/0216752 A1 Jul. 18, 2019

Related U.S. Application Data

(63) Continuation of application No. PCT/KR2017/000915, filed on Jan. 25, 2017.

(30) Foreign Application Priority Data

Sep. 22, 2016 (KR) .................. 10-2016-0121577

(51) Int. Cl.
| | | |
|---|---|---|
| *A23L 33/10* | (2016.01) | |
| *A61K 31/165* | (2006.01) | |
| *A61K 49/00* | (2006.01) | |
| *A61P 25/28* | (2006.01) | |
| *A61P 29/00* | (2006.01) | |
| *A61P 25/16* | (2006.01) | |
| *A61K 31/155* | (2006.01) | |
| *A61K 31/16* | (2006.01) | |
| *A61K 31/352* | (2006.01) | |
| *C07D 311/86* | (2006.01) | |

(52) U.S. Cl.
CPC ............ *A61K 31/165* (2013.01); *A23L 33/10* (2016.08); *A61K 31/155* (2013.01); *A61K 31/16* (2013.01); *A61K 31/352* (2013.01); *A61K 49/0041* (2013.01); *A61P 25/16* (2018.01); *A61P 25/28* (2018.01); *A61P 29/00* (2018.01); *C07D 311/86* (2013.01); *A23V 2002/00* (2013.01); *A23V 2200/322* (2013.01)

(58) Field of Classification Search
None
See application file for complete search history.

(56) References Cited

U.S. PATENT DOCUMENTS

| | | |
|---|---|---|
| 4,439,450 A | 3/1984 | Coleman |
| 2006/0142181 A1 | 6/2006 | Miller |
| 2014/0112978 A1 | 4/2014 | Su et al. |

OTHER PUBLICATIONS

International Search Report issued in PCT/KR2017/000915; dated Jun. 21, 2017.
Zhao, Y. et al., "Design, Synthesis and Biological Evaluation of Brain Targeting L-ascorbic Acid Prodrugs of Ibuprofen with 'Lock-in' Function", European Journal of Medicinal Chemistry, 2014, vol. 82, pp. 314-323.
Pinnen, F. et al., "Ibuprofen and Glutathione Conjugate as a Potential Therapeutic Agent for Treating Alzheimer's Disease", Arch Pharm Chemistry in Life Sciences, 2011, vol. 11, pp. 139-148.
Biswas. G. et al., "Synthesis of Ibuprofen Conjugated Molecular Transporter Capable of Enhanced Brain Penetration", Journal of Chemistry, Electronic publication date Jan. 16, 2017, vol. 2017, article ID 4746158, pp. 1-10.

*Primary Examiner* — James W Rogers
(74) *Attorney, Agent, or Firm* — Studebaker & Brackett PC

(57) ABSTRACT

The present invention relates to an ibuprofen conjugate in which ibuprofen (S-(+)-ibuprofen) is covalently linked to a guanidine-terminal-group-bound sugar alcohol derivative and to a pharmaceutical composition containing the same. The ibuprofen conjugate in which ibuprofen is covalently linked to a guanidine-terminal-group-bound sugar alcohol derivative can more effectively penetrate into the brain by passing through the blood-brain barrier (BBB), thus enabling efficient drug delivery to the brain, whereby administration of the ibuprofen conjugate in an optimal dose can minimize side effects of nonsteroidal anti-inflammatory drugs (NSAIDs) and can prevent or treat degenerative brain disease.

6 Claims, 5 Drawing Sheets
(3 of 5 Drawing Sheet(s) Filed in Color)

PHARMACEUTICAL COMPOSITION FOR PREVENTING OR TREATING DEGENERATIVE BRAIN DISEASE

CROSS REFERENCE TO RELATED APPLICATIONS

The present application is a Continuation of International Application No. PCT/KR2017/000915 filed on Jan. 25, 2017, which claims priority to Korean Patent Application No. 10-2016-0121577 filed on Sep. 22, 2016. The entire contents of which is incorporated herein for all purposes by this reference.

TECHNICAL FIELD

The present invention relates to a pharmaceutical composition for preventing or treating degenerative brain disease, containing an ibuprofen conjugate as an active ingredient, and to an ibuprofen conjugate compound.

BACKGROUND ART

Nonsteroidal anti-inflammatory drugs (NSAIDs), which are drugs that reduce pain and inflammation, are widely used for alleviating symptoms such as headaches, osteoarthritis, rheumatoid arthritis, low back pain and musculoskeletal disease. Furthermore, these drugs have been reported to have the effects of ameliorating neurodegenerative disease, such as Alzheimer's disease and Parkinson's disease, as well as suppressing brain damage caused by inflammatory reactions by blocking neuroinflammatory pathways.

Most nonsteroidal anti-inflammatory drugs act by inhibiting cyclooxygenase (COX), which is involved in the biosynthesis of prostaglandin. Cyclooxygenase includes two kinds of enzymes, namely cyclooxygenase-1 (COX-1) and cyclooxygenase-2 (COX-2), in which COX-1 is involved in the synthesis of prostaglandin, which is normally produced to maintain the biological function in the human body. Specifically, COX-1 plays a role in synthesizing prostaglandin to maintain the function of each organ in the gastrointestinal tract, kidneys, and platelets, and is present in vascular endothelial cells, gastric mucosa and the kidneys and has a gastric mucosal protective action or a homeostatic function to regulate renal blood flow. Additionally, COX-2 is expressed by inflammatory cells during inflammation and synthesizes prostaglandin, which causes inflammation, to thus induce inflammation at the inflamed site and maintain inflammation.

Examples of isotypes derived from prostaglandin include thromboxane ($TXA_2$), showing platelet aggregation action, and prostacyclin ($PGI_2$), showing platelet aggregation inhibitory action. Thromboxane is produced by COX-1 and prostacyclin is produced by COX-2. Typical nonsteroidal anti-inflammatory drugs are non-selective inhibitors that inhibit both COX-1 and COX-2, and may cause not only anti-inflammatory effects due to COX-2 inhibition but also gastrointestinal side effects such as gastritis, gastric ulcers, perforation, and gastrointestinal bleeding due to COX-1 inhibition. On the other hand, COX-2 selective inhibitors that selectively inhibit COX-2 reduce gastrointestinal side effects caused by inhibition of COX-1, but selectively inhibit prostacyclin without inhibiting thromboxane, thereby causing platelet aggregation, undesirably resulting in cardiovascular side effects.

Ibuprofen is a propionic acid derivative and is the most commonly used non-aspirin non-steroidal anti-inflammatory agent that may be purchased in most countries without a prescription. Long-term use of ibuprofen may delay Alzheimer's disease and reduce the risk of developing Parkinson's disease. A study found that people who took ibuprofen on a regular basis had 38% less risk of developing Parkinson's disease than those taking other non-steroidal anti-inflammatory drugs.

However, such nonsteroidal anti-inflammatory drugs have limited ability to penetrate the brain due to the blood-brain barrier. The blood-brain barrier present in the cerebral blood vessels is a barrier separating the cerebrospinal fluid from the blood, and has high selective permeability and thus functions to protect the brain from harmful substances. However, this blood-brain barrier has hampered the development of brain-related therapies by blocking the passage of drugs for treating brain disease such as tumors, Alzheimer's disease, and Parkinson's disease, as well as harmful substances. Meanwhile, ibuprofen is ionized into anions at a physiological pH and binds to plasma proteins extensively, thus staying in the body for a long time and circulating in the body, resulting in the drug being distributed throughout an increased volume. Thereby, only a small amount of ibuprofen reaches the brain, and thus a large dose thereof is required to increase the efficacy of the drug. Moreover, long-term use of ibuprofen may also cause side effects such as cardiovascular and gastrointestinal disorders. Therefore, it is necessary to develop ibuprofen that is effective at preventing and alleviating neurodegenerative disease through penetration into the brain through the blood-brain barrier even when used in a small dose.

Technical Solution

The present invention provides a compound represented by Chemical Formula 1 below and a pharmaceutical composition for the prevention or treatment of brain disease containing the same.

<Chemical Formula 1>

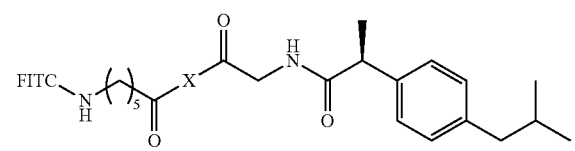

{in Chemical Formula 1, X is represented by Chemical Formula 2 below:

<Chemical Formula 2>

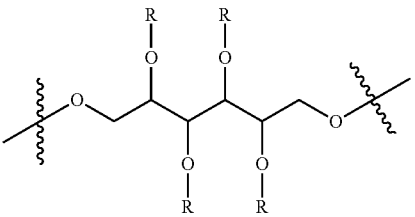

wherein Rs are hydrogen, deuterium or Chemical Formula 3 below, Rs including at least one Chemical Formula 3 below:

<Chemical Formula 3>

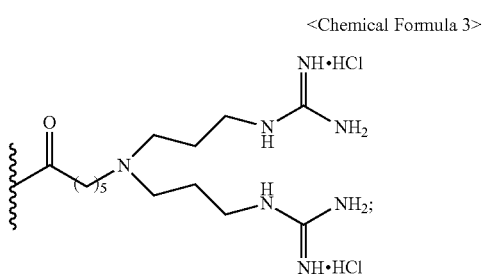

and

FITC represents a fluorescein group.}

Preferably, the present invention provides a compound of Chemical Formula 1, in which X represents a sugar alcohol having carbon atoms, particularly any one selected from the group consisting of sorbitol, mannitol, galactitol, fucitol, iditol, and inositol, and a pharmaceutical composition containing the same. More preferably, sorbitol or mannitol is used.

The compound of the present invention is effective at treating brain disease, such as stroke, palsy, dementia, Alzheimer's disease, Parkinson's disease, Lou Gehrig's disease, Huntington's disease, Pick's disease, Creutzfeldt-Jakob disease, thrombosis, embolism, transient ischemic attack, lacune, multiple sclerosis, proximal lateral sclerosis, palsy, stroke, mild cognitive impairment, cerebral hemorrhage, cerebral infarction, head trauma, cerebral circulation metabolic disorder, and brain coma.

Advantageous Effects

According to the present invention, a compound and a pharmaceutical composition enable efficient drug delivery to the brain through a blood-brain barrier (BBB), thereby minimizing side effects and inhibiting and preventing the progression of degenerative brain disease. Also, the prodrug method provided by the present invention can be useful in other nonsteroidal anti-inflammatory drugs (NSAIDs).

DESCRIPTION OF DRAWINGS

The patent or application file contains at least one drawing executed in color. Copies of this patent or patent application publication with color drawing(s) will be provided by the Office upon request and payment of the necessary fee.

FIG. 2A shows the confocal laser scanning microscopy image, and FIG. 2B shows the differential interference contrast image of HeLa cells treated with Compound 8 (ibuprofen conjugate) according to an embodiment of the present invention. FIG. 2C shows the merged image of FIG. 2A and FIG. 2B, and FIG. 2D shows the confocal laser scanning microscopy image and FIG. 2E shows the differential interference contrast image of HeLa cells treated with Compound 9 (control) (Scale bar: 20 μm).

DETAILED DESCRIPTION

Figure 1:
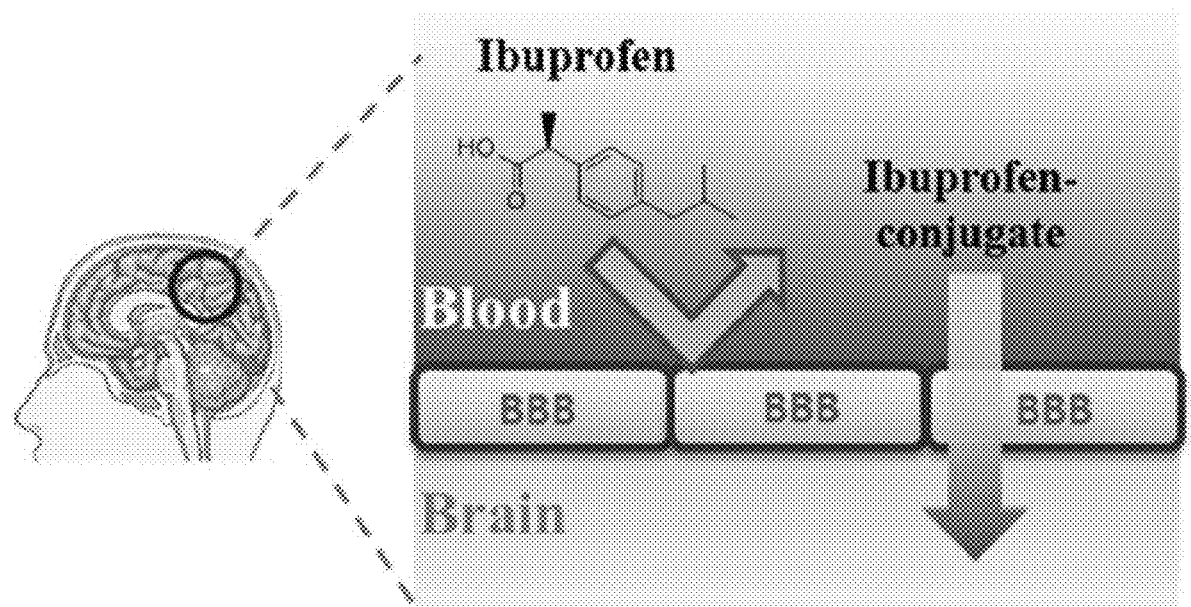
FIG. 1 schematically shows an ibuprofen conjugate that passes through the blood-brain barrier (BBB), which prevents intracellular internalization of ibuprofen in the brain.
Figure 2A:
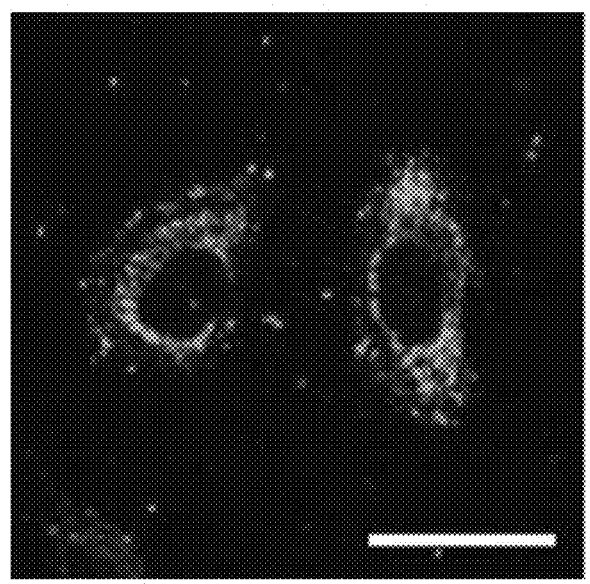
FIGS. 2A-2E show the results of cellular uptake of Compound 8 and Compound 9 in HeLa cells.
Figure 2B:
Figure 2C:
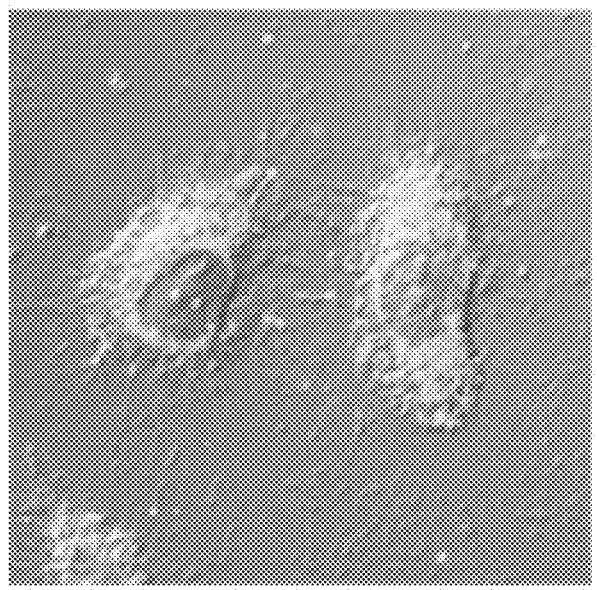
Figure 2D:
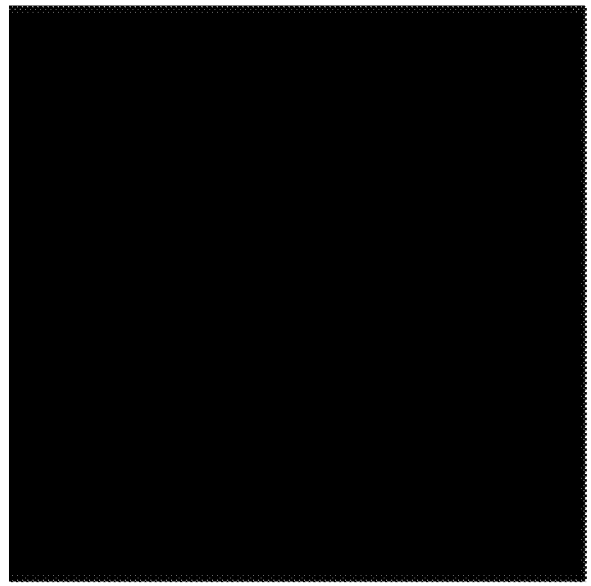
Figure 2E:
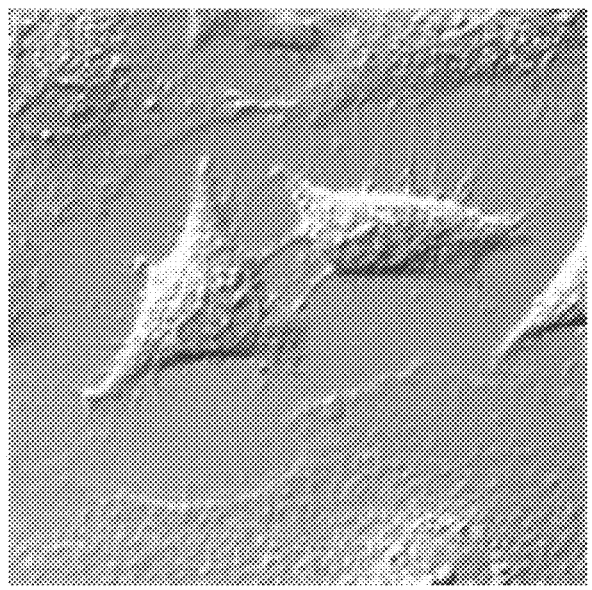

A better understanding of the constructions and effects of the present invention will be given through the following examples, which are merely set forth to illustrate the present invention but are not to be construed as limiting the scope of the present invention. Furthermore, it is to be understood that the scope of the present invention is set forth by the accompanying claims, and that all the technical ideas within the range equivalent thereto are incorporated into the scope of the invention.

Synthesis Example 1

I. Synthesis of (S)-2-(2-(4-isobutylphenyl)propanamido)acetic acid (2)

The compound according to the present invention, represented as Compound 2, may be synthesized through Scheme 1 below, and the present invention is not limited thereto.

<Scheme 1>

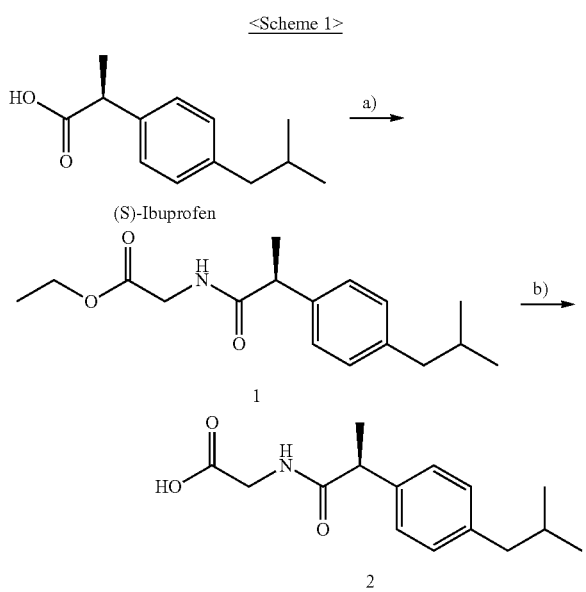

a) Glycine ethylester, HCl, EDC, DMAP, DMF, Et$_3$N
b) LiOH, THF-H$_2$O (5:1)

1. Synthesis of (S)-ethyl-2-(2-(4-isobutylphenyl)propanamido)acetate (1)

(S)-(+)-ibuprofen (140 mg, 0.68 mmol), glycine ethylester hydrochloride (104 mg, 0.75 mmol), EDC (195 mg, 1.02 mmol), triethylamine (1.04 ml, 0.748 mmol), and DMAP (42 mg, 0.34 mmol) were added to DMF (2 ml) and stirred at room temperature in a nitrogen atmosphere for 24 hr. After completion of the reaction, the resulting solution was treated with ethyl acetate and then washed several times with a saturated NaHCO$_3$ aqueous solution, distilled water and brine. The organic layer was dried over Na$_2$SO$_4$ and then concentrated, and the resulting compound was purified through silica gel column chromatography, thus obtaining Compound 1 (199 mg, 99%) as a colorless liquid.

R$_f$: 0.54 (Hexane:EtOAc=7:3); $^1$H-NMR (in CDCl$_3$, δ) 0.99 (d, J=6.6 Hz, 6H), 1.23 (t, J=6.9 Hz, 3H), 1.51 (d, J=7.2 Hz, 3H), 1.84 (m, 1H), 2.44 (d, J=7.2 Hz, 2H), 3.60 (q, J=7.2 Hz, 1H), 3.94 (dd, J=5.4, 12.6 Hz, 2H), 4.15 (q, J=6.9 Hz, 2H), 7.11 (d, J=8.1 Hz, 2H), 7.22 (d, J=8.1 Hz, 2H); $^{13}$C-NMR (in CDCl$_3$, δ) 13.9, 18.3, 22.2, 30.0, 41.3, 44.9, 46.2, 61.1, 127.2, 129.4, 138.1, 140.5, 169.7, 174.5; MS (FAB) [M+H]$^+$ calculated for C$_{17}$H$_{25}$NO$_3$ m/z 292.18, found 292.20.

2. Synthesis of (S)-2-(2-(4-isobutylphenyl)propanamido)acetic acid (2)

Compound 1 (195 mg, 0.67 mmol) and lithium hydroxide (16 mg, 0.67 mmol) were added to 6 ml of a mixed solution of THF and H$_2$O (5:1) and stirred at room temperature for 36 hr. After completion of the reaction, evaporation in a vacuum, extraction with EtOAc and washing with saturated 1N HCl, distilled water and brine were performed. The organic layer was dried over Na$_2$SO$_4$ and then concentrated, and the resulting compound was purified through silica gel column chromatography, thereby yielding Compound 2 (105 mg, 60%) as a white solid.

R$_f$: 0.12 (Hexane:EtOAc=7:3); m.p. 87-90° C.; $^1$H-NMR (in CDCl$_3$, δ) 0.88 (d, J=6.6 Hz, 6H), 1.49 (d, J=7.2 Hz, 3H), 1.83 (m, 1H), 2.43 (d, J=7.2 Hz, 2H), 3.62 (q, J=7.2 Hz, 1H), 3.94 (dd, J=5.4, 18.3 Hz, 2H), 6.35 (m, 1H, NH), 7.09 (d, J=8.1 Hz, 2H), 7.18 (d, J=8.1 Hz, 2H); MS (FAB) [M+H]$^+$ calculated for C$_{15}$H$_{21}$NO$_3$ m/z 264.15, found 264.17.

Synthesis Example 2

I. Synthesis of 1-O-(2-aminoacetoxy-ibuprofen)-2,3,4,5-tetra-O—[N-{bis-(3-guanidinopropyl)}-6-aminohexanoyl]-6-O-[6-(fluoresceinyl-5-thioureido)-hexanoyl]-D-sorbitol 8HCl (8)

The compound according to the present invention, represented as Compound 8, may be synthesized through Scheme 2 below, and the present invention is not limited thereto.

<Scheme 2>

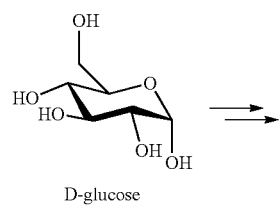

D-glucose

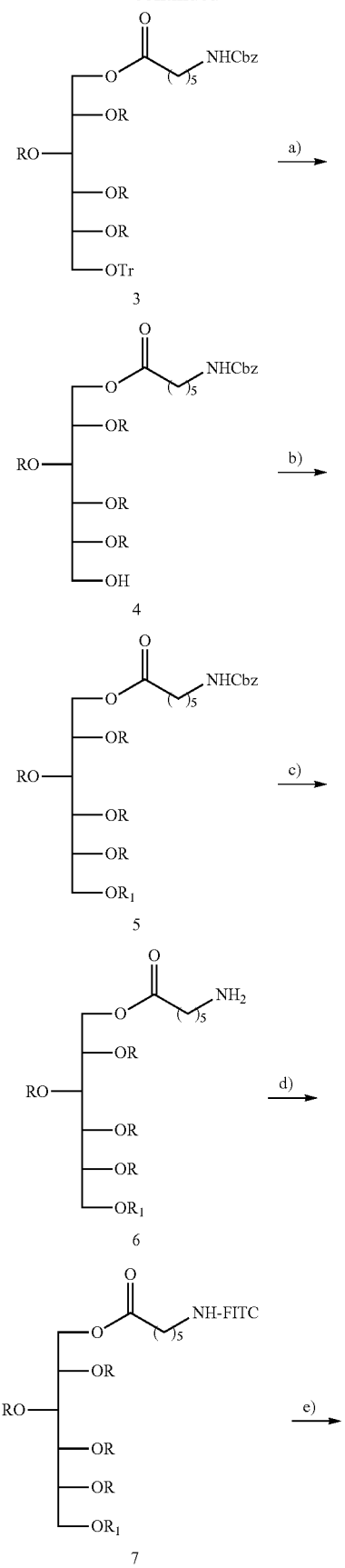

-continued

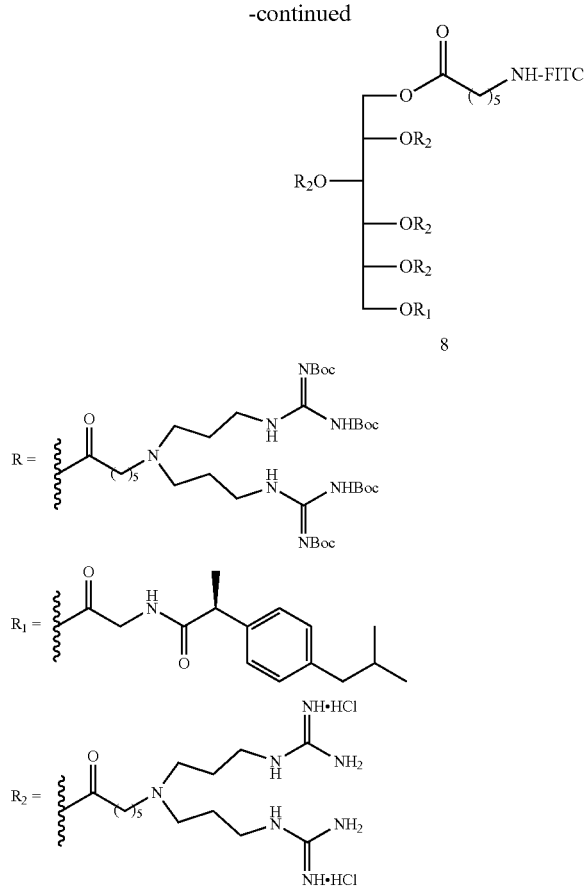

a) SiO₂ with hexane-1% TFA, hexane-1% Et₃N
b) Compound 2, EDC, DMAP, DMF
c) 10% Pd/C, H₂ (g) (50 psi), MeOH—CH₂Cl₂ (9:1)
d) FITC-I, Et₃N, THF, EtOH
e) HCl (g) in EtOAc 1. Synthesis of 1-O-trityloxy-2,3,4,5-tetra-O—(N-{bis-[3-(N',N"-bis-Boc-guanidino)-propyl]}-6-aminohexanoyl)-6-O—(N-Cbz-6-aminohexanoyl)-D-sorbitol (3)

D-glucose was subjected to continuous coupling with Cbz-protected aminocaproic acid and reduced to acetylated sorbitol, thus obtaining Compound 3.

2. Synthesis of 1-O—(N-Cbz-6-aminohexanoyl)-2,3,4,5-tetra-O—(N-{bis-[3-(N',N"-bis-Boc-guanidino)-propyl]}-6-aminohexanoyl)-6-O-D-sorbitol (4)

The lower portion of a silica gel column was packed with hexane containing 1% triethylamine and the upper portion thereof was packed with hexane containing 1% TFA (trifluoroacetic acid) so that the sea sand layer was located between two solvents. Compound 3 (98 mg, 0.028 mmol) was dissolved in $CH_2Cl_2$ containing 1% TFA and sonicated for several seconds, and the resulting solution was introduced into the column and then eluted with $CH_2Cl_2$ and MeOH in a manner in which the amount of MeOH in $CH_2Cl_2$ was increased, thus obtaining Compound 4 (66 mg, 73%) as colorless solid foam.

3. Synthesis of 1-O-(2-aminoacetoxy-ibuprofen)-2,3,4,5-tetra-O—(N-{bis-[3-(N',N"-bis-Boc-guanidino)-propyl]}-6-aminohexanoyl)-6-O—(N-Cbz-6-aminohexanoyl)-D-sorbitol (5)

A solution of Compound 4 (90 mg, 0.027 mmol) dissolved in DMF (2 ml) at room temperature was added with Compound 2 (10.7 mg, 0.041 mmol), EDC (11 mg, 0.054 mmol), and DMAP (2 mg, 0.016 mmol) and then stirred in a nitrogen atmosphere for 48 hr. After completion of the reaction, the resulting solution was concentrated under reduced pressure. The residue was dissolved in EtOAc and washed several times with a saturated $NaHCO_3$ aqueous solution, distilled water and brine. The organic layer was dried over $Na_2SO_4$ and then concentrated, and the resulting compound was purified through silica gel column chromatography, thus obtaining Compound 5 (50 mg, 52%) as white solid foam.

$R_f$: 0.46 ($CH_2Cl_2$:MeOH=10:1); $^1$H-NMR (in $CDCl_3$, δ) 0.88-0.90 (m, 6H), 1.25-1.69 (m, 193H), 2.32-2.45 (m, 32H), 3.08-3.50 (m, 18H), 3.61-3.71 (m, 2H), 3.97-4.29 (m, 4H), 4.85-5.12 (m, 4H), 5.02 (s, 2H), 5.33 (m, 1H), 7.09-7.12 (m, 2H), 7.22-7.27 (m, 2H), 7.33 (m, 5H), 8.49-8.57 (m, 8H), 11.40 (m, 8H); $^{13}$C-NMR (in $CDCl_3$, δ) 14.1, 18.6, 22.4, 22.7, 24.0, 24.3, 24.6, 26.3, 28.0, 28.1, 28.3, 28.3, 29.4, 29.7, 30.2, 31.9, 38.0, 39.0, 45.1, 49.9, 53.2, 66.5, 79.2, 79.8, 83.7, 118.3, 122.6, 127.2, 127.4, 127.7, 127.9, 128.0, 128.5, 128.7, 129.5, 129.7, 136.7, 138.7, 140.5, 143.3, 153.0, 153.1, 156.2, 156.5, 156.8, 162.9, 163.5, 170.3, 172.6, 172.8, 174.3, 181.6

4. Synthesis of 1-O-(2-aminoacetoxy-ibuprofen)-2,3,4,5-tetra-O—(N-{bis-[3-(N',N"-bis-Boc-guanidino)-propyl]}-6-aminohexanoyl)-6-O-D-sorbitol (6)

A solution of Compound 5 (45 mg, 0.013 mmol) in a mixed solution of $CH_2Cl_2$ and MeOH ($CH_2Cl_2$:MeOH=1:9, 10 ml) was hydrogenated at room temperature for 12 hr with 10% Pd/C (25 mg) under 50 psi. The catalyst was filtered and the filtrate was evaporated, thus obtaining Compound 6 (38 mg, 88%) as a clear sticky liquid amino compound.

$^1$H-NMR (in $CDCl_3$, δ) 0.88-0.90 (m, 6H), 1.25-1.77 (m, 193H), 2.25-2.45 (m, 32H), 3.09-3.50 (m, 18H), 3.61-3.71 (m, 2H), 4.01-4.29 (m, 4H), 4.85-5.12 (m, 4H), 5.33 (m, 1H), 7.09-7.12 (m, 2H), 7.22-7.27 (m, 2H), 8.56 (brs, 8H), 11.39 (brs, 8H)

5. Synthesis of 1-O-(2-aminoacetoxy-ibuprofen)-2,3,4,5-tetra-O—[N-{bis-(3-(N',N"-bis-Boc-guanidino)-propyl]}-6-aminohexanoyl]-6-O-[6-(fluoresceinyl-5-thioureido)-hexanoyl]-D-sorbitol (7)

A solution of Compound 6 (38 mg, 0.011 mmol) dissolved in a mixed solution of THF and absolute ethanol (THF:absolute ethanol=1:2, 3 ml) was added with fluorescein-5-isothiocyanate (FITC) (6.5 mg, 0.017 mmol) and triethylamine (4.6 μl, 0.033 mmol), stirred at room temperature for 36 hr in a dark room and then concentrated in a vacuum. After completion of the reaction, the resulting product was purified through silica gel column chromatography, thus obtaining Compound 7 (25 mg, 60%) as a greenish yellow-colored sticky solid.

$R_f$: 0.42 ($CH_2Cl_2$:MeOH=10:1); $^1$H-NMR (in $CDCl_3$, δ) 0.88-0.90 (m, 6H), 1.25-1.85 (m, 193H), 2.31-2.44 (m, 32H), 3.09-3.48 (m, 18H), 3.66 (m, 2H), 4.15-4.29 (m, 4H), 4.88-5.07 (m, 4H), 5.34 (m, 1H), 6.51-7.32 (m, 11H), 7.73 (m, 1H), 8.04 (m, 1H), 8.57 (brs, 8H), 11.39 (brs, 8H)

6. Synthesis of 1-O-(2-aminoacetoxy-ibuprofen)-2,3,4,5-tetra-O—[N-{bis-(3-guanidinopropyl)}-6-aminohexanoyl]-6-O-[6-(fluoresceinyl-5-thioureido)-hexanoyl]-D-sorbitol 8HCl (8)

A solution of Compound 7 (20 mg, 0.005 mmol) dissolved in EtOAc (1 ml) at room temperature was added with EtOAc (5 ml) saturated with HCl (g), stirred for 24 hr, and then concentrated. The residue was washed with a mixed solution of diethyl ether and MeOH (diethyl ether:MeOH=20:1), dried, and purified through reverse phase C-8 silica gel ($H_2O/CH_3CN$=1:1 to 1:2 with 0.1% TFA) MPLC. The purified product was dissolved in deionized water, filtered through a PTFE syringe filter, and lyophilized, thereby yielding Compound 8 (7.6 mg, 58%) as greenish yellow-colored solid foam (HCl salt).

Analytical HPLC (ZORBAX SB-C8): $t_R$=2.8 min (flow rate: 1 $cm^3$ $min^{-1}$; UV=220 nm; isocratic $CH_3CN:H_2O$=40:60), purity 85+%; UV ($H_2O$): $\mu_{max}$ 492 nm, e=18,333 $cm^{-1}M^{-1}$); $^1$H-NMR (in MeOD, δ) 0.89-0.91 (m, 6H), 1.01-1.80 (m, 45H), 2.00-2.09 (m, 16H), 2.38-2.43 (m, 16H), 3.29-3.32 (m, 16H, partially overlapped with $CD_3OD$ peak), 3.48-3.88 (m, 6H), 4.03-4.55 (m, 9H), 5.00-5.41 (m, 2H), 6.66-6.78 (m, 6H), 7.09-7.34 (m, 4H), 7.70 (m, 1H), 7.80 (m, 1H), 8.06 (m, 1H); MALDI-TOF-MS $[M+Na]^+$ calculated for $C_{104}H_{171}N_{31}O_{18}SNa$ m/z 2198.30, found 2198.96.

Synthesis Example 3

I. Synthesis of fluoresceinyl (S)-2-(2-(4-isobutylphenyl)propanamido)-acetate (9)

The compound according to the present invention, represented as Compound 9, may be synthesized through Scheme 3 below, and the present invention is not limited thereto.

<Scheme 3> a) aminofluorescein, EDC, DMAP, DMF

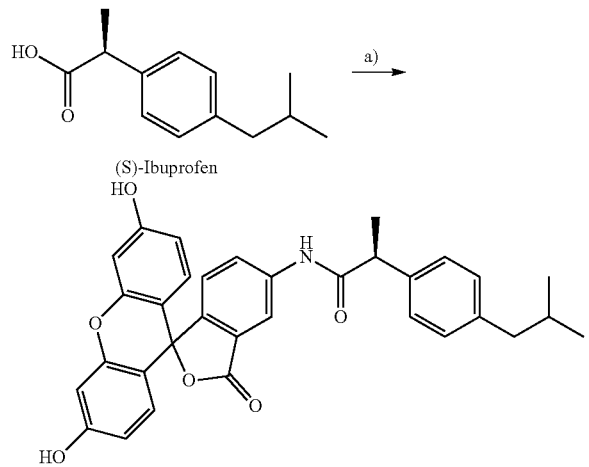

1. Synthesis of fluoresceinyl (S)-2-(2-(4-isobutylphenyl)propanamido)-acetate (9)

(S)-(+)-ibuprofen (70 mg, 0.34 mmol), fluorescein amine (129 mg, 0.37 mmol), EDC (97 mg, 0.51 mmol), and DMAP (21 mg, 0.17 mmol) were added to DMF (2 ml) and stirred at room temperature in a nitrogen atmosphere for 24 hr. After completion of the reaction, the resulting solution was treated with EtOAc and then washed several times with a saturated $NaHCO_3$ aqueous solution, distilled water and brine. The organic layer was dried and concentrated, and the resulting compound was purified through silica gel column chromatography, thereby yielding Compound 9 (140 mg, 77%) as a yellow sticky liquid.

$R_f$: 0.54 ($CH_2Cl_2$:MeOH=10:1); $^1$H-NMR (in $CDCl_3$, δ) 0.90 (d, J=6.6 Hz, 6H), 1.59 (d, J=7.2 Hz, 3H), 1.85 (m, 1H), 2.46 (d, J=7.2 Hz, 2H), 6.54-6.72 (m, 4H), 6.78-6.95 (m, 4H), 7.11 (m, 3H), 7.28 (m, 2H); $^{13}$C-NMR (in $CDCl_3$, δ) 18.7, 22.7, 30.5, 31.8, 36.9, 45.3, 45.5, 103.2, 108.7, 110.3, 110.3, 110.8, 113.0, 117.2, 117.2, 117.7, 122.7, 124.9, 127.5, 128.3, 129.3, 129.4, 129.9, 137.2, 141.2, 142.9, 148.7, 152.2, 152.3, 152.6, 159.5, 163.1, 170.3, 173.2; MS (FAB) $[M+H]^+$ calculated for $C_{33}H_{29}NO_6$ m/z 535.20, found 535.19.

Example

I. Evaluation of Cellular Uptake of Ibuprofen Conjugate

1. Cell Culture

HeLa cells were cultured at 37° C. in wet air containing 5% $CO_2$ in a DMEM (high-glucose Dulbecco's Modified Eagle's Medium) containing penicillin-added 10% (v/v) FBS (fetal bovine serum). Subculturing was performed every 2 to 3 days until the cells became subconfluent.

2. Evaluation of Cellular Uptake

HeLa cells (1×10⁵ cells per well) were seeded on a 35 mm coverglass dish (SPL Ltd., Korea) and cultured for 24 hr, after which the medium was removed, and the HeLa cells were washed with cold PBS (×1) (Dulbecco's phosphate buffered saline, pH 7.4). The resulting cells were cultured at 37° C. for 30 min in 3 ml of DMEM containing 10 μM Compound 8 or 10 μM Compound 9, after which the medium was removed, and the HeLa cells were washed five times with cold PBS. The intracellular internalization and intracellular localization of the compound were investigated through fluorescence, achieved using fluorescein, using a confocal laser scanning microscope (Olympus Fluoview FV1000, N.A. 1.30, 40×, planApo, oil immersion lens). The fluorescence of FITC was analyzed at an excitation wavelength of 488 nm and an emission wavelength of 500 to 530 nm, and all experiments were performed three times.

FIGS. 2A-2E shows strong green fluorescence that is predominant in the cytoplasm, which means that Compound 8 is capable of diffusing efficiently into the cytoplasm through the cell membrane. In contrast, Compound 9 did not show fluorescence in the cells. Therefore, it was confirmed that the guanidine portion of the conjugate structure is essential for the delivery of ibuprofen into cells.

II. In-Vivo Distribution of Mouse Tissue

Compound 8 or 9 (94.6 mg $kg^{-1}$) was dissolved in sterilized distilled water (500 μl), and each solution was injected intraperitoneally into 8-week-old mice (C57BL/6, 22 g). After 20 min, the mice administered with the above solution were perfused with PBS (pH 7.4) containing paraformaldehyde (4%), and the main organs (brain, heart, lungs, kidneys, spleen and liver) thereof were cultured overnight in PBS (phosphate buffered saline) containing sucrose (0.5 M). A cryoprotectant was added thereto and the above tissue was cut into 15 μm flakes using a cryostat, transferred to a coated slide glass and then dried. Each flake was washed with PBS, treated with Triton X-100 (0.3%) at room temperature for 15 min, and analyzed using an Axioplan2 fluorescence imaging microscope. As a control, deionized water (500 μl) was injected into other mice, and the same procedures as above were performed, after which the compound represented by green fluorescence of FITC in each tissue was compared with autofluorescence of the control. All mouse experiments were conducted at POSTECH animal facilities in compliance with relevant laws and institutional guidelines.

Figure 3:
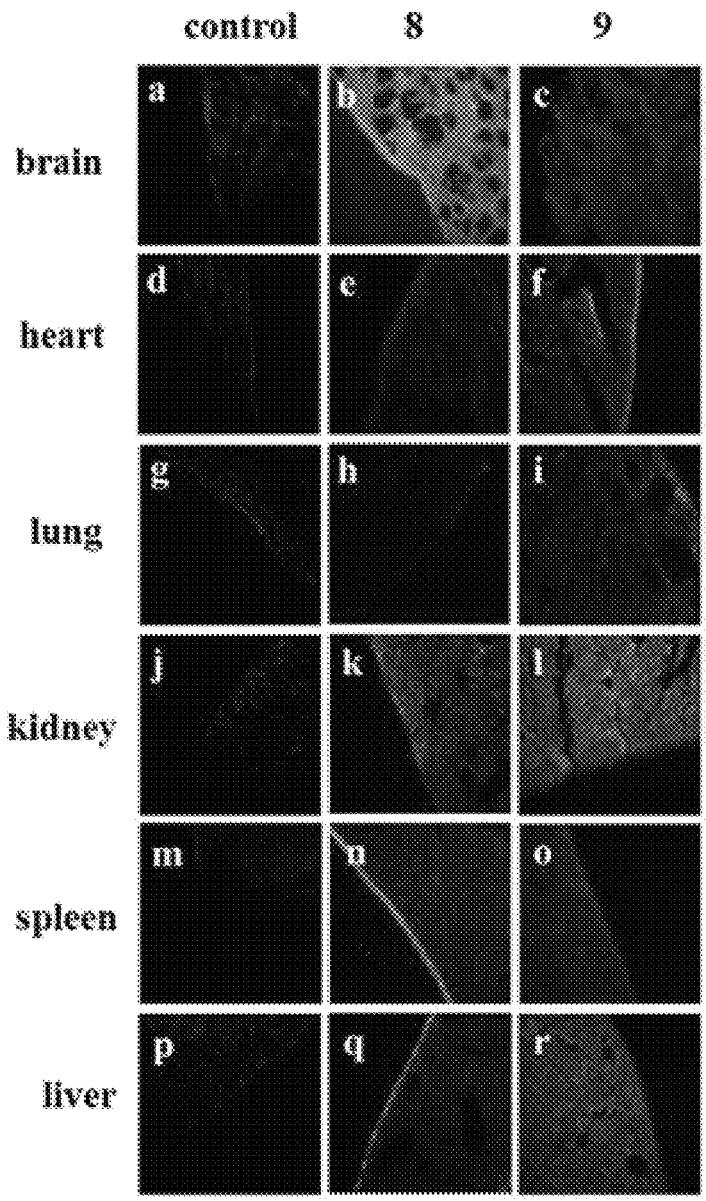
FIG. 3 shows fluorescence images of mouse tissue flakes separated from mice 20 min after intraperitoneal injection into mice according to an embodiment of the present invention, (a) and (b) illustrating the brain, (c) and (d) illustrating the heart, (e) and (f) illustrating the lungs, (g) and (h) illustrating the kidneys, (i) and (j) illustrating the spleen, and (k) and (l) illustrating the liver, with the distribution of Compound 8 (middle), a control (left) and Compound 9 (right) in mouse tissue (exposure time (ms): brain 5000, heart 1000, lung 5000, kidney 2000, spleen 2000, and liver 2000, $\lambda_{max}$=488 nm (green fluorescence from FITC))

As shown in FIG. 3, Compound 8 was mainly distributed in the brain and kidneys, and was then observed in the spleen and liver, but was not observed in the heart or lungs. This result indicates that the conjugate is capable of easily passing through the blood-brain barrier (BBB) and thus is capable of penetrating into the brain of the mouse. Similarly, Compound 9 was tested in the same manner but was found to be not distributed in the brain. This indicates that the guanidine-rich portion of Compound 8 forms a noncovalent bond on the surface of brain cells via hydrogen bonding with a charge pair, after which Compound 8 passes through the blood-brain barrier via endocytosis.

III. Plasma Stability Test

In order to evaluate plasma stability, a homogeneous solution of Compound 8 (500 g ml$^{-1}$) was prepared. An aliquot thereof was injected into the plasma (human, Sigma, USA) so as to reach a final concentration of 50 μg/ml, followed by vortexing and culturing at 37° C. for 0, 3, 6, 9, 12, 15, 18, 21 and 24 hr. The plasma solution (200 μl) was then mixed with 1 ml of MeOH to prevent hydrolysis of Compound 8. This solution was added with biotin (internal standard) in distilled water (100 μl, 5 μg/ml) and centrifuged at 2000 rpm for 10 min. The supernatant was collected and dried in air. The residue was dissolved in distilled water (2 ml) and centrifuged at 2000 rpm for 10 min. The supernatant thus obtained was analyzed using HPLC through the following method.

IV. HPLC Analysis

10 μl of the clean supernatant obtained through the above method was introduced into the HPLC system. The UV detector was set at 260 nm and the flow rate was 1.0 ml/min for a running time of 10 to 15 min. The isocratic mobile phase system consisted of MeOH/H$_2$O (30/70), and the column oven was maintained at 37° C. using a C18-column (Agilent, ZORBAX, 4.6×250 mm, 5 μm).

HPLC chromatograms were obtained at each interval, and the remaining amount of Compound 8 was calculated and expressed as a percentage by subtracting the concentration of ibuprofen, released based on the area under the curve, from the sum of the initial concentration of Compound 8 and the internal standard.

Figure 4:
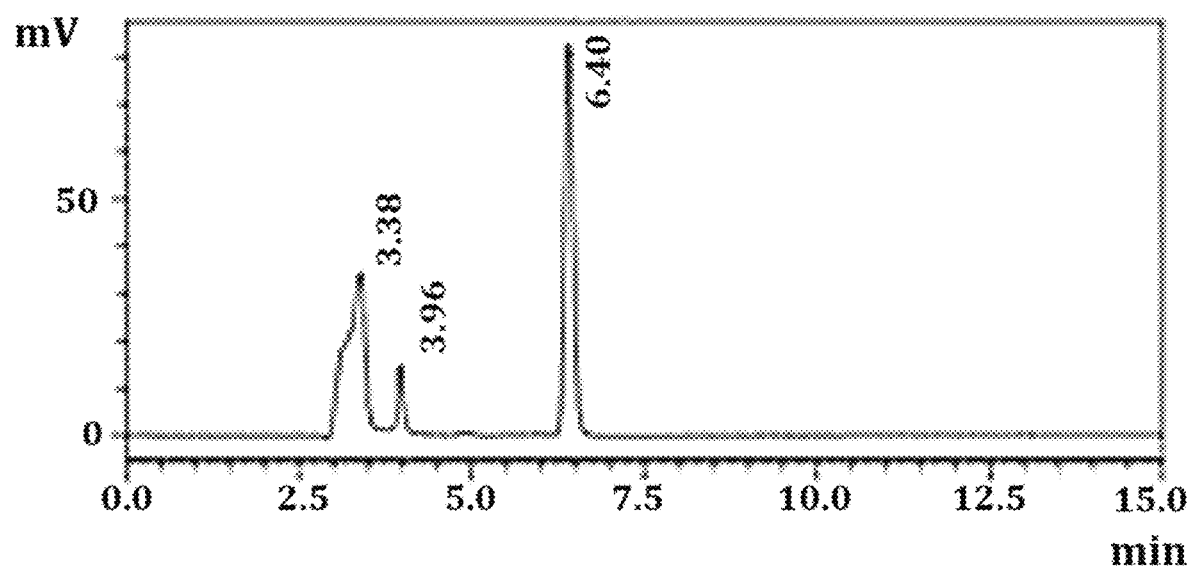
FIG. 4 shows the HPLC chromatograms of biotin (internal standard) and Compound 8 after culture for 3 hr in plasma (retention time of biotin and plasma: 3.38 min, Compound 8: 6.40 min)
Figure 5:
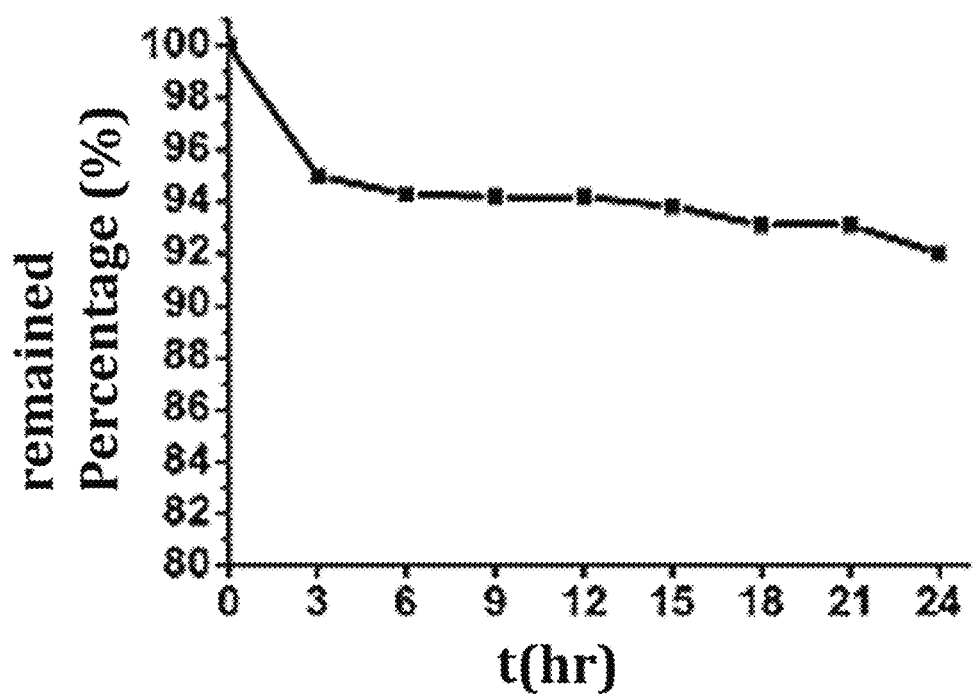
FIG. 5 shows the percentage of Compound 8 remaining in the plasma after the culture time.

The samples detected at 260 nm showed slight shifts in individual retention times, and the released ibuprofen was identified as a retention time peak at 3.96 min (FIG. 4). After culture for 3 hr, Compound 8 underwent about 5% hydrolysis relative to the initial time (0 hr). Over time, however, the amount remaining gradually decreased by ~8% for the next culture time of 21 hr (FIG. 5). This means that Compound 8 has a long half-life and considerable stability in the plasma, indicating that the likelihood of the compound reaching the BBB is higher.

The invention claimed is:

1. A pharmaceutical composition for treating a brain disease, containing, as an active ingredient, a compound represented by Chemical Formula 1 below:

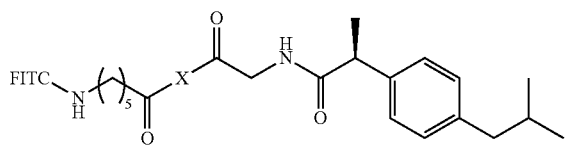

wherein X is represented by Chemical Formula 2 below:

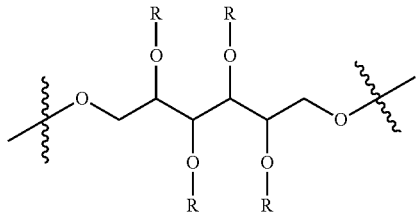

wherein the R groups are selected from the group consisting of hydrogen, deuterium or Chemical Formula 3 below:

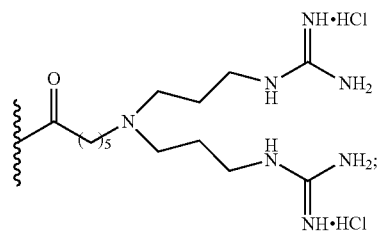

wherein at least one R is Chemical Formula 3, and FITC represents a fluorescein group.

2. The pharmaceutical composition of claim 1, wherein all of the R groups are represented by Chemical Formula 3.

3. The pharmaceutical composition of claim 1, wherein the brain disease is selected from the group consisting of stroke, palsy, dementia, Alzheimer's disease, Parkinson's disease, Lou Gehrig's disease, Huntington's disease, Pick's disease, Creutzfeldt-Jakob disease, thrombosis, embolism, transient ischemic attack, lacune, multiple sclerosis, proximal lateral sclerosis, palsy, stroke, mild cognitive impairment, cerebral hemorrhage, cerebral infarction, head trauma, cerebral circulation metabolic disorder, and brain coma.

4. A compound represented by Chemical Formula 1 below:

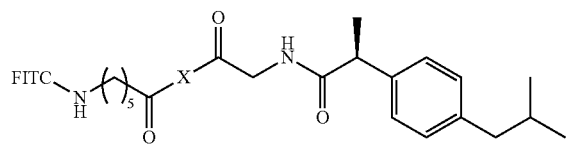

wherein X is represented by Chemical Formula 2 below:

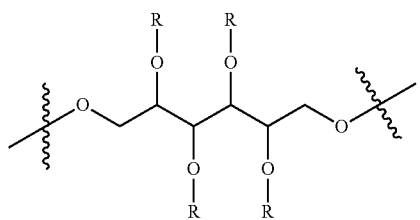

wherein the R groups are selected from the group consisting of hydrogen, deuterium or Chemical Formula 3 below:

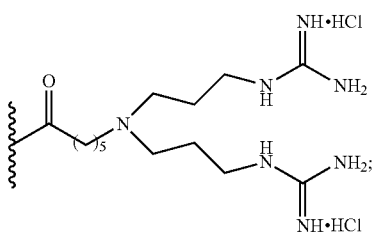

wherein at least one R is chemical formula 3, and FITC represents a fluorescein group.

5. The compound of claim 4, wherein all of the R groups are represented by Chemical Formula 3.

6. A health functional food composition for treating a degenerative brain disease, comprising the compound of claim 4.

* * * * *